United States Patent
Plihal et al.

(10) Patent No.: US 10,338,004 B2
(45) Date of Patent: Jul. 2, 2019

(54) PRODUCTION SAMPLE SHAPING THAT PRESERVES RE-NORMALIZABILITY

(71) Applicant: KLA-Tencor Corporation, Milpitas, CA (US)

(72) Inventors: Martin Plihal, Pleasanton, CA (US); Ankit Jain, Ballston Spa, NY (US); Michael Lennek, San Jose, CA (US)

(73) Assignee: KLA—Tencor Corp., Milpitas, CA (US)

( * ) Notice: Subject to any disclaimer, the term of this patent is extended or adjusted under 35 U.S.C. 154(b) by 326 days.

(21) Appl. No.: 14/666,942

(22) Filed: Mar. 24, 2015

(65) Prior Publication Data
US 2015/0276618 A1 Oct. 1, 2015

Related U.S. Application Data

(60) Provisional application No. 61/971,040, filed on Mar. 27, 2014.

(51) Int. Cl.
*G01N 21/93* (2006.01)
*G01N 21/95* (2006.01)
*H01L 21/66* (2006.01)

(52) U.S. Cl.
CPC ......... *G01N 21/93* (2013.01); *G01N 21/9501* (2013.01); *H01L 22/12* (2013.01);
(Continued)

(58) Field of Classification Search
CPC ............... G01N 21/93; G01N 21/9501; G01N 2201/063; G01N 2201/12; H01L 22/12; H01L 22/20; G01R 31/28
(Continued)

(56) References Cited

U.S. PATENT DOCUMENTS

| | | | |
|---|---|---|---|
| 6,265,232 B1 * | 7/2001 | Simmons | H01L 22/20 257/E21.525 |
| 7,997,073 B2 * | 8/2011 | Keuper | E02F 9/2228 60/422 |

(Continued)

FOREIGN PATENT DOCUMENTS

WO 2010/093733 8/2010

OTHER PUBLICATIONS

International Search Report for PCT/US2015/022833 dated Jul. 14, 2015.
U.S. Appl. No. 14/614,202, filed Feb. 4, 2015 by Plihal et al.

*Primary Examiner* — Dzung Tran
(74) *Attorney, Agent, or Firm* — Ann Marie Mewherter

(57) ABSTRACT

Methods and systems for generating defect samples are provided. One method includes identifying a set of defects detected on a wafer having the most diversity in values of at least one defect attribute and generating different tiles for different defects in the set. The tiles define a portion of all values for the at least one attribute of all defects detected on the wafer that are closer to the values for the at least one attribute of their corresponding defects than the values for the at least one attribute of other defects. In addition, the method includes separating the defects on the wafer into sample bins corresponding to the different tiles based on their values of the at least one attribute, randomly selecting defect(s) from each of two or more of the sample bins, and creating a defect sample for the wafer that includes the randomly selected defects.

43 Claims, 4 Drawing Sheets

(52) U.S. Cl.
CPC ........ *H01L 22/20* (2013.01); *G01N 2201/063* (2013.01); *G01N 2201/12* (2013.01)

(58) Field of Classification Search
USPC ............. 257/82, 182, E21.53; 438/5, 14, 22; 702/35, 108, 82, 182, E21.53, 40; 700/289
See application file for complete search history.

(56) References Cited

U.S. PATENT DOCUMENTS

| | | |
|---|---|---|
| 8,948,494 B2 | 2/2015 | Plihal et al. |
| 2001/0023083 A1 | 9/2001 | Simmons |
| 2007/0088451 A1* | 4/2007 | Akram .................. G03F 7/7065 700/121 |
| 2008/0129988 A1 | 6/2008 | Saito et al. |
| 2009/0000995 A1* | 1/2009 | Yanai .................. G01R 31/2894 209/557 |
| 2009/0287440 A1 | 11/2009 | Kulkarni et al. |
| 2010/0081217 A1 | 4/2010 | Nagano |
| 2013/0035876 A1* | 2/2013 | Huang ............... G01N 21/9501 702/40 |
| 2014/0133737 A1* | 5/2014 | Plihal .................. G06T 7/0008 382/149 |

\* cited by examiner

PRODUCTION SAMPLE SHAPING THAT PRESERVES RE-NORMALIZABILITY

BACKGROUND OF THE INVENTION

1. Field of the Invention

This invention generally relates to methods and systems for creating a detect sample for a wafer that is suitable for production monitoring and can be re-normalized to a total defect population detected on the wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

During production runs, in order to monitor the defectivity of production wafers, typically a sample of defects is created from a total defect population detected on a wafer. That sample of defects is then manually classified (i.e. classification performed by a human expert) one of several possible techniques such as reviewing the sampled defects on a defect review tool such as a scanning electron microscope (SEM). The classification results can then be extrapolated back to defects that are similar to the sampled defects in some manner.

There are three main approaches to production sampling. The first is random sampling in which defects are randomly selected from the detected population. This sampling is a re-normalizable sampling scheme that is very easy to setup, but it is not very efficient in capturing lower count defect types. In some instances, random sampling may rely on spatial diversification by requiring that dies and dusters are not sampled excessively. This spatial diversification introduces subtle bias into the renormalization process, which results in systematic errors that are different for different wafers and that are difficult to correct.

The second is class code based sampling in which defects are selected randomly from bins. This method requires a defect binner (classifier) to be trained and executed on the inspection results. Compared to random sampling, this method is more stable and efficient for well performing binners. The increased efficiency and stability are achieved through the partial diversification provided by the binners. This sampling is re-normalizable. Just as in the case of random sampling, spatial diversification is also typically enforced.

The third is rule-based sampling in which defects are selected based on a set of rules. This scheme is a hybrid scheme that has very similar characteristics to class code based sampling. This sample is also re-normalizable as long as the defects are sampled randomly from the set of defects that satisfy each rule.

There are two main disadvantages of the existing sampling methods. For example, the resulting samples tend to have significant fluctuations from run-to-run even for relatively stable processes. In addition, the sampling tends to be less effective in selecting relatively low count defect types, thus lacking critical information relatively frequently. The existing sampling methods also have a number of secondary disadvantages. For instance, the existing methods require tuning classifiers for class code based sampling. In addition, the classifiers themselves require periodic performance monitoring.

Accordingly, it would be advantageous to develop systems and/or methods for generating a defect sample for a wafer that do not have one or more of the disadvantages described above.

SUMMARY OF THE INVENTION

The following description of various embodiments is not to be construed in any way as limiting the subject matter of the appended claims.

One embodiment relates to a computer-implemented method for generating a defect sample for a wafer. The method includes acquiring inspection results for the wafer. The inspection results include information for defects detected on the wafer by an inspection process. The information includes information for one or more attributes of the defects. The method also includes identifying a set of the defects having the most diversity in values of at least one of the one or more attributes and generating different tiles for different defects in the set. Generating the different tiles includes generating a tile for a first defect in the set. The tile defines a portion of all of the values for the at least one attribute of all of the defects detected on the wafer. The values in the portion are closer to the values for the at least one attribute of the first defect than the values for the at least one attribute of other defects in the set. Generating the different tiles also includes repeating the generating the tile step for one or more of the other defects. In addition, the method includes separating the defects detected on the wafer into sample bins corresponding to the different tiles based on the values of the at least one attribute of the defects and the portions of the values defined by the different tiles. The method further includes randomly selecting one or more defects from each of two or more of the sample bins and creating a detect sample for the wafer including the randomly sampled defects. The acquiring, identifying, generating the different tiles, separating, randomly selecting, and creating steps are performed by a computer system.

The method described above may be performed as described further herein. In addition, the method described above may include any other step(s) of any other method(s) described herein. Furthermore, the method described above may be performed by any of the systems described herein.

An additional embodiment relates to a non-transitory computer-readable medium storing program instructions executable on a computer system for performing a computer-implemented method for generating a detect sample for a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to generate a defect sample for a wafer. The system includes an inspection subsystem configured to acquire inspection results for the wafer. The inspection results include information for defects detected on the wafer by an inspection process performed by the inspection subsystem, and the information includes information for one or more attributes of the defects. The system also includes a computer subsystem configured for performing the identifying, generating the different tiles, separating, randomly selecting, and creating steps described above. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
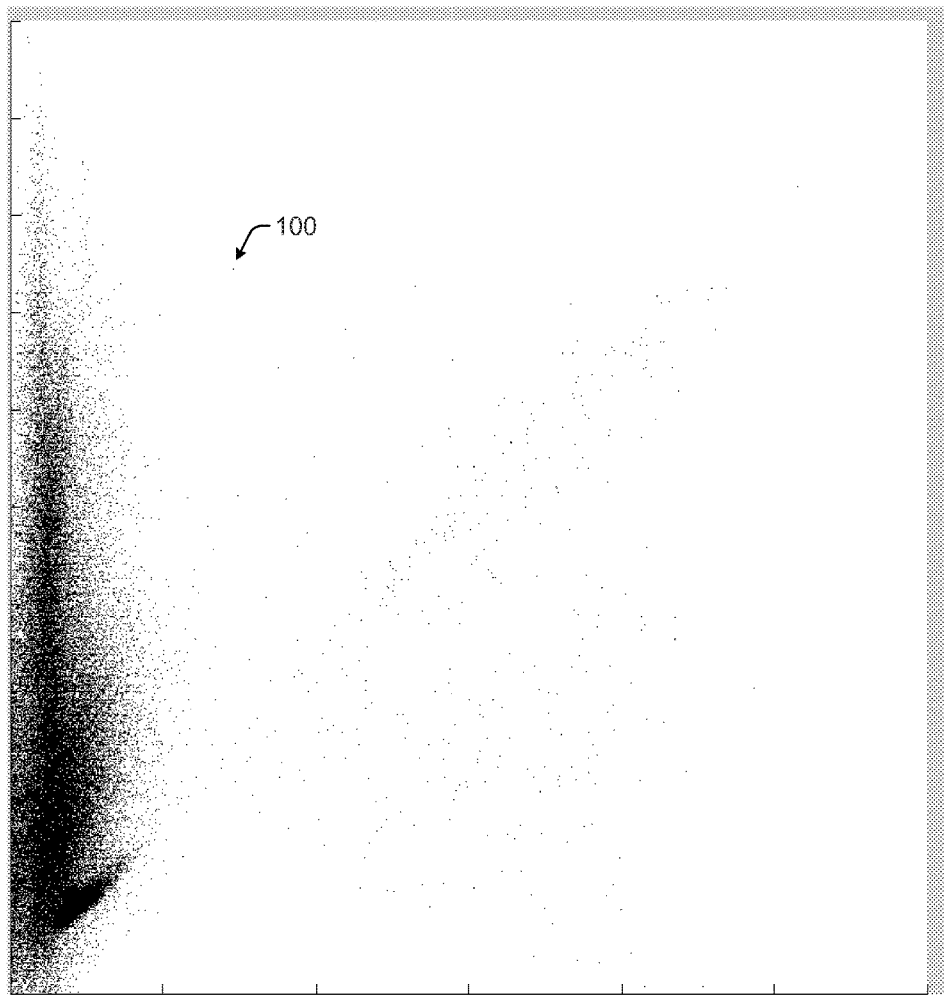
FIG. 1 is a scatter plot of data points corresponding to values for two attributes determined for defects detected on a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for generating a defect sample for a wafer. As described further herein, the embodiments are particularly suitable for production sampling. For example, the main goal of production sampling is to monitor process stability by getting a representative cross section of wafer defectivity. In order to achieve this goal, production sampling must have two important properties: (a) the sample contains the maximum number of defect types detected on the wafer, and (b) it is re-normalizable so that reliable estimates of defect counts for each defect type are available for excursion monitoring.

The embodiments described herein provide new production sampling methods that have the above-described two properties and have the following benefits over existing methods. In particular, the embodiments described herein are more efficient than existing methods in finding defect types. The embodiments described herein are also more stable than existing methods. In addition, the embodiments described herein do not require setting up and tuning defect classifiers for defect type monitoring. Furthermore, the embodiments described herein adjust themselves to the noise floor variations. Moreover, the embodiments described herein, at the same time as providing all of the above-noted advantages, provide statistically unbiased estimates of the defect counts for all the sampled defect types, making excursion monitoring (statistical process control (SPC)) by type possible.

The embodiments described herein are, therefore, strikingly different from existing production sampling methods in that they provide true diversity sampling with various biasing capabilities and yet provide statistically unbiased samples that can be used for re-normalization. In this manner, the embodiments described herein are different from some currently available diversity sampling schemes, because the other schemes do not provide unbiased estimates of overall defectivity by defect type.

The method includes acquiring inspection results for the wafer. A user may select the inspection results file to be used in the method. The inspection results include information for defects detected on the wafer by an inspection process. The information includes information for one or more attributes of the defects. The one or more defect attributes may include any defect attributes that can be determined by an inspection system or from results generated by an inspection system. Examples of suitable defect attributes that can be used as described further herein include, but are not limited to, energy, magnitude, die coordinates, and design attributes. The inspection results may include any other suitable information about the defects detected on the wafer such as the locations of the defects detected on the wafer and image data or images generated for the defects.

The inspection process may include any suitable inspection process that can be performed by any suitable inspection system. In one embodiment, the wafer is a production wafer, and the inspection process is performed for production monitoring. For example, as noted above, the embodiments described herein are particularly suitable for creating defect samples that can be used for production monitoring. The wafer inspection system may be further configured as described herein.

The term "production" as used herein is intended to have the normal and customary meaning in the context of semiconductor device manufacturing. For example, "production"

in the context of semiconductor device manufacturing tends to refer to the high volume manufacturing of semiconductor devices that is typically performed after some sort of ramp up stage of fabrication.

The method includes identifying a set of the defects having the most diversity in values of at least one of the one or more attributes. Identifying the set of defects having the most diversity in at least one attribute may be performed as described in commonly assigned U.S. Pat. No. 8,948,494 issued on Feb. 3, 2015 to Plihal et al. and U.S. patent application Ser. No. 14/614,202 filed Feb. 4, 2015 by Plihal et al., which are incorporated by reference as if fully set forth herein. The embodiments described herein build upon the attribute-based diversity sampling described in this patent and patent application. This diversity sampling scheme was first introduced for defect discovery, and it has shown significant value both for defect discovery and for classifier setup. For example, this diversity sampling is showing significant value in its ability to capture defect types and produce relatively stable samples from wafer-to-wafer.

In one embodiment, the at least one attribute does not include only positions of the defects on the wafer. For example, as noted above, some currently used methods for sampling such as random sampling and class-code based sampling are performed based on spatial positions of the defects on the wafer to avoid oversampling from certain defect clusters or dies. Those currently used methods therefore can achieve a certain measure of spatial diversification among the sampled defects. However, the currently used methods for sampling are not able to diversify the sampled defect population with respect to any other defect attributes. Therefore, unlike the embodiments described herein, the currently used sampling methods do not intentionally diversify with respect to position and do not diversify with respect to any other defect attributes.

The embodiments described herein propose a number of changes to the diversity sampling scheme to make it hilly production worthy thereby creating a new paradigm for production sampling. For example, the embodiments described herein leverage the attribute-based diversity sampling to produce diverse (and possibly biased) samples according to user specifications. In one such example, FIG. 1 is a scatter plot in which each individual point 100 corresponds to a defect in a population detected on a wafer. The horizontal axis corresponds to one defect attribute, and the vertical axis corresponds to another defect attribute. Therefore, the values of the two defect attributes for a defect determine the location of the point for that defect in the plot. Since two defect attributes are used to generate the scatter plot, the scatter plot is a two-dimensional (2D) scatter plot, and the attribute space used for various steps described herein is a 2D attribute space. As such, FIG. 1 shows a 2D representation of the defect distribution. However, the attribute space may be only a one-dimensional (1D) attribute space if only one defect attribute is used in the embodiments described herein or it can defined by the values for 3 or more attributes.

Figure 2:
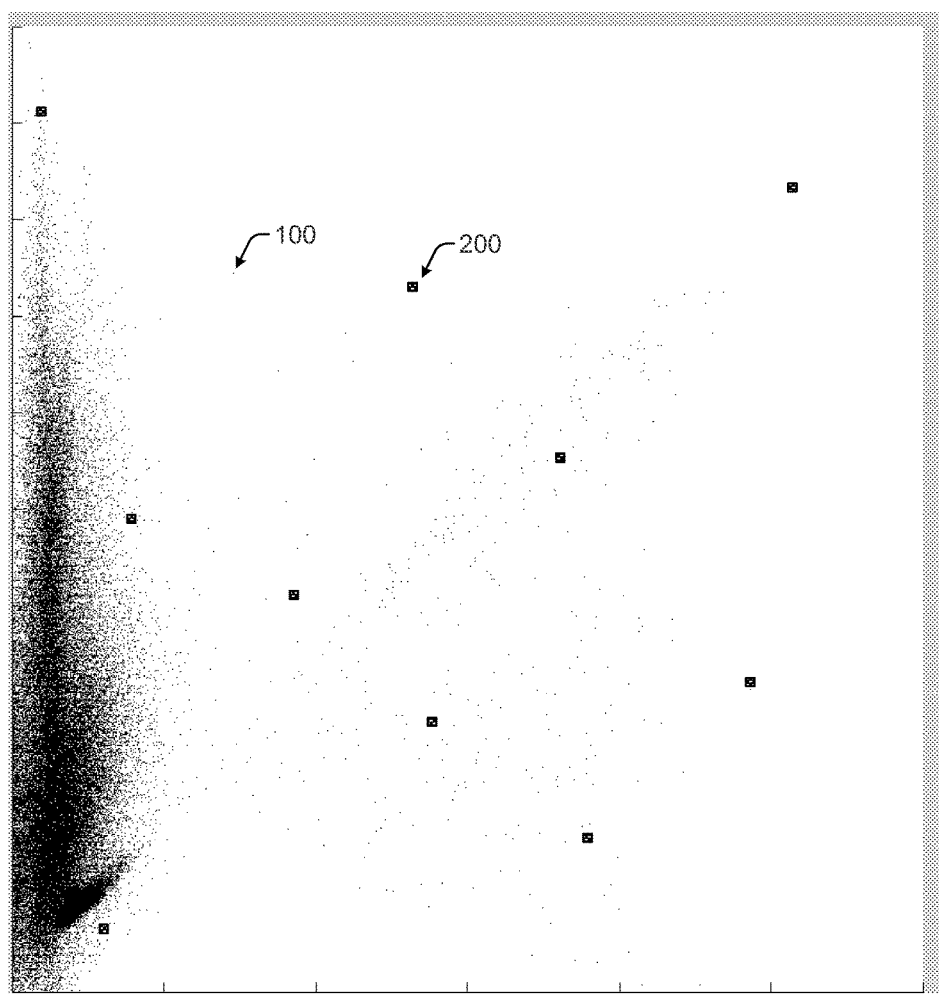
FIG. 2 is the scatter plot of FIG. 1 in which some defects have been identified according to embodiments described herein as having the most diversity in the values of at least one of the attributes.

FIG. 2 is the scatter plot of FIG. 1 showing defects 200 that have been identified as having the most diversity in the values of the two defect attributes. Therefore, FIG. 2 shows a sample of the defects (i.e., a subset of all of the defects detected on the wafer) produced by diversity sampling. It is noted that defects 200 may not actually have the most diversity in the two values. Instead, these defects 200 are merely illustrative examples of some of defects 100 that may or may not have the most diversity in the two defect attributes. In addition, although a certain number of identified defects 200 are shown in FIG. 2, it is to be understood that the number of identified defects may include any suitable number and may be selected, for example, by a user. FIG. 2 also shows how diversity sampling can sample defects in an attribute space to produce a diverse sample while suppressing sampling from the high density region of the scatter plot.

The method also includes generating different tiles for different defects in the set. In this manner, instead of actually sampling the defects identified by diversity sampling, the method generates tiling of the entire attribute space used for diversity sampling. Generating the different tiles includes generating a tile for a first defect in the set. The tile defines a portion of all of the values for the at least one attribute of all of the defects detected on the wafer, and the values in the portion are closer to the values for the at least one attribute of the first defect than the values for the at least one attribute of other defects in the set. In other words, the tiles are determined by the condition of proximity of the attribute values to the attribute values of the sampled defects. In other words, all values of the attribute(s) in tile k are closer to the attribute values of the $k^{th}$ sampled defect than to the attribute values of any other sampled defect. Generating the tiles in this manner may be performed using any suitable mathematical algorithms known in the art that can be modified for or applied to the datasets described herein (i.e., defect attribute values). For example, the tiles that are generated as described herein may be similar mathematically to a Voronoi diagram. Therefore, the mathematical algorithms and/or processes used to produce a Voronoi diagram may be adapted to the inspection results for the defects to generate the tiles for the defects.

Generating the different tiles also includes repeating the generating the tile step for one or more of the other defects. In this manner, each tile may be individually generated for each defect identified by diversity sampling. In one embodiment, a number of the different tiles that are generated is equal to a number of the defects in the set. In other words, for a sample of size N, there will be N tiles. In this manner, there may be exactly one tile created for each of the defects in the set of most diverse defects.

Figure 3:
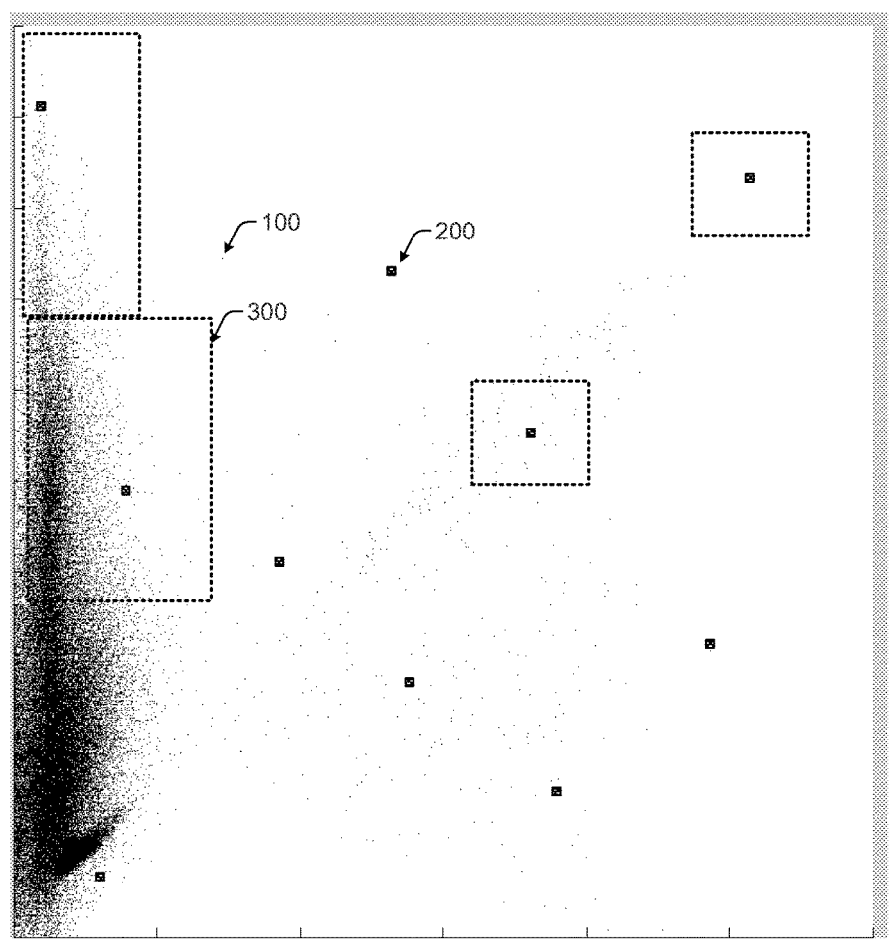
FIG. 3 is the scatter plot of FIG. 2 showing different tiles that have been generated according to embodiments described herein for some of the identified defects.

The tiles described above correspond to sample bins. In addition, the method includes separating the defects detected on the wafer into sample bins corresponding to the different tiles based on the values of the at least one attribute of the defects and the portions of the values defined by the different tiles. For example, as shown in FIG. 3, tiles 300 may be generated for different diversity sampled defects 200. In other words, a tile may be generated for each sampled defect such that the attribute value(s) for a sampled defect is/are only located within a single tile. In addition, although tiles are not shown in FIG. 3 for each of the diversity sampled defects, this is only for the sake of clarification. In general, it will be desirable to create a tile for each of the diversity sampled defects. As shown in FIG. 3, different tiles will encompass different portions of the attribute space (e.g., depending on the values of the attribute(s) for the diversity sampled defects). In addition, since the tiles are generated based on the values of the attribute(s) that are closer to the attribute(s) of a diversity sampled defect, the tiles will generally not overlap in the attribute space (i.e., the same value(s) of attribute(s) cannot be closer to more than one defect).

Each of the tiles shown in FIG. 3 therefore corresponds to a sample bin, and each of the defects having attribute value(s) within a tile can be separated into the corresponding sample bin. In this manner, each tile and its corresponding sample bin represents a subset of the defects that "belong" to the nearest sampled defect. For example, all of the defects within a tile shown in FIG. 3 will be assigned to its corresponding sample bin. As such, all defects in tile k will be closer to the $k^{th}$ sampled defect than to any other sampled defect.

Since the sample bins are created based on the defect population detected on a wafer, the sample bins are created dynamically (i.e., on a wafer-to-wafer basis). In this manner, the sample bins are not tuned bins and are not produced by a tuned defect classifier. Therefore, the embodiments described herein are advantageous in that they do not require setting up and tuning defect classifiers for defect type monitoring.

The method further includes randomly selecting one or more defects from each of two or more of the sample bins. In one embodiment, an average number of the one or more defects randomly selected from each of the two or more of the sample bins is selected by a user. In this manner, the average number of defects to be sampled from a sample bin can be a user-configurable parameter. In addition, the sample budget can be distributed across the bins either equally or proportionally. In other words, in one embodiment, the method includes determining a number of the one or more defects to be randomly selected from each of the two or more of the sample bins by dividing a total number of defects to be included in the created defect sample equally across the sample bins. In a different embodiment, the method includes determining a number of the one or more defects to be randomly selected from each of the two or more of the sample bins by dividing a total number of defects to be included in the created defect sample proportionally across the sample bins. In a further embodiment, the method includes determining a number of the one or more defects to be randomly selected from each of the two or more of the sample bins by dividing a total number of defects to be included in the created defect sample semi-proportionally across the sample bins. In semi-proportional distribution of the sample across the sample bins, each sample bin may get sampled at least once and any excess sample size gets distributed proportionally to defect count in the bins.

Alternatively, in another embodiment, the method includes determining a number of the one or more defects to be randomly selected from each of the two or more of the sample bins based on a total number of defects to be included in the created defect sample and a predetermined confidence level for using the created defect sample to re-normalize the defects detected on the wafer by the inspection process. In this manner, the sampling can be configured with a target for sample size, and the desired confidence level for re-normalization estimates. The method may then allocate sample size per bin to best achieve this confidence level within the budget.

In one embodiment, the randomly selecting described above is performed for one of the two or more sample bins such that each defect in the one sample bin has an equal probability of being selected. For example, randomly selecting defects from the sample bins may be performed with equal probability for all defects in the bin. In another embodiment, the randomly selecting described above is performed for one of the two or more sample bins such that at least two defects in the one sample bin have different probabilities of being selected. For example, randomly selecting defects from sample bins with equal probability for all defects in the bin can be replaced with random sampling where the probability of sampling each defect is itself determined by biasing, prioritization, etc.

The method also includes creating a defect sample for the wafer that includes the randomly selected defects. For example, information for all of the randomly selected defects sampled from all of the bins may be combined together into a single file thereby creating a defect sample. The created defect sample may be output as an inspection results file that can be used by any other method or system or can be used by the methods and systems described herein. The inspection results file that includes the created defect sample may also include any information generated for the created defect sample by the embodiments described herein possibly in combination with an other information from the original inspection results file including any of that used by the embodiments described herein. If the created defect sample is to be used for renormalization, the file that includes the information for the created defect sample may also include the sample bin label on all the other detected defects, so that the number of defects can be counted. Alternatively, it would be possible to export the sampled defects with the sample bin code along with the information about how many defects were detected in each sample bin.

In one embodiment, the method includes classifying (e.g., manually classifying) the randomly selected defects in the defect sample and re-normalizing the defects detected on the wafer with results of the classifying step and total number of defects in each of the sample bins thereby determining estimates of defect counts for different defect types detected on the wafer in the inspection process. Re-normalization may be achieved by treating the sample bins the same way that any other re-normalization process would. In other words, once the defect sample is created, the resulting defect sample bins may be re-normalized using any existing method. In one such example, the total number of defects of type i may be determined by the following formula:

$$N_i = \sum_{k=1}^{N_B} \frac{N_k}{n_k} n_{k,i}$$

where $N_B$=number of dynamic bins (sample bins), i denotes defect type i, $N_i$=number of defects of type i on the wafer (this is the estimate), $N_k$=total number of defects in bin k, $n_k$=number of sampled defects in bin k, and $n_{k,i}$=number of sampled defects of type i in bin k. In some embodiments, the method includes performing production monitoring based on the re-normalized defects. In other words, the re-normalized defects may be used for production monitoring just as any other re-normalized defects would.

The embodiments described herein are, therefore, different from currently used methods and systems for creating defect samples. For example, in many existing methods, defect types are binned using a classifier that has been tuned on a training wafer. A fixed number of defects is then randomly sampled from each bin, and that fixed number may be determined during setup. A number of detected defects of each type may then be estimated from the sample.

In contrast, in the embodiments described herein, diversification (and possibly biasing) criteria for sampling may be specified. The sample bins may then be created dynamically on the inspected data. In this manner, the sample bins adapt to the data and encode the diversification (and possibly biasing) criteria. Defects are then randomly selected from the sample bins. The number of detected defects of each type can then be estimated from the sample using the dynamically created sample bins.

In this manner, both the old and new methods may start with the results of an inspection of a wafer. However, since the currently used methods typically separate the defects detected on the wafer into bins using a previously created and tuned classifier, any differences between the training wafer and the inspected wafer can cause some defects to be binned incorrectly. As such, random sampling from those bins, as is currently performed, can miss certain defect types (e.g., the ones that were binned incorrectly). In contrast, since the embodiments described herein create the sample bins using information about defects detected on the wafer being inspected dynamically based on diversification (and possibly biasing) criteria, the resulting diversified (and possibly biased) sample captures more defect types than the previously used methods. As a result, when estimating the defect population from the created sample in the currently used methods, renormalization can fail on un-sampled defect types white, in the embodiments described herein, renormalization is possible and the sample is more stable and has better DOI coverage than that which was previously achievable.

The embodiments described herein have, therefore, a number of advantages over old methods for creating a defect sample. For example, sample shaping (diversification and possibly biasing) is achieved by generating sample bins during the first pass sampling. In addition, outlier defects will have a substantially small number of defects in their corresponding sample bins, and, in some cases, will even be alone in their sample bins as shown by the tile in FIG. 3 that is closest to the upper right hand corner of the scatter plot. In other words, some tiles (or sample bins) will include only a few defects (or even only one defect) while other tiles may include a great many defects. In general, outlier detects will be characterized by relatively low tile populations. This means that randomization of sampling from tiles (sample bins) will not have a significant effect on the outlier population in the created defect sample. Therefore, randomization will not significantly degrade the sample shaping (diversification and possibly biasing) encoded in the sample bins. Superior sample shaping capabilities make the sampling schemes described herein more efficient in finding defects of interest (DOIs) while maintaining the sample re-normalizability (meaning the ability to get unbiased statistical estimates of defect type counts in the population). An additional advantage is that the renormalization error can be controlled by modifying the average number of defects to be sampled per sample bin, and by changing how this average number is distributed across the sample bins, e.g. equally or semi-proportionally to the bin population. In other words, the idea of allowing multiple defects to be sampled from each sample bin makes it possible to control the error on statistical estimates. Controlling the bounds on re-normalization error dynamically (by variable sample size) is believed to be new.

In another example of an advantage of the embodiments described herein, excursions in a particular defect type will typically show up as increased defect density in some part of the attribute space. This increased density will not be detected by the sample itself due to the diversification criteria, which prevents nearby defects to be sampled multiple times until the rest of the space has been explored. However, this increased density will show up as a spike in the defect count in the corresponding sample bin. Therefore, the excursion will be detectable when compared with corresponding sample bins generated for other wafers. Only one of the defects in a sample bin that has increased density may be sampled with or without the excursion, but the additional defects will belong to the same sample bin and therefore will show up as a spike during re-normalization. Therefore, examination of the fluctuations in sample bin populations gives extra insight into potential excursions unlike "static" sample binning methods. In this manner, the method may include performing production monitoring based on a number of defects separated into at least one of the sample bins.

In another embodiment, the identifying and generating the different tiles steps automatically adjust the created defect sample to a noise floor of the inspection process. In other words, the embodiments described herein adjust themselves to the noise floor variations. Therefore, another advantage of the embodiments described herein is that the sampling approaches described herein effectively achieve dynamic binning sensitive to the noise floor, where the number of bins is equal to the number of diverse samples. In an additional embodiment, the identifying and generating the different tiles steps automatically adjust the created defect sample to wafer-to-wafer variations of the inspection process. In particular, since the embodiments described herein create the tiles and their corresponding sample bins based on the defect population detected on a wafer when creating a defect sample for that wafer, the embodiments described herein will be relatively immune to changes from wafer to wafer in the defect population. Therefore, the embodiments described herein provide superior stability of the sample with respect to scan-to-scan variations, as well as with respect to systematic shifts in noise floor.

The embodiments described herein can also be executed from within any existing sampling software or systems (after suitable modifications of that software or those systems). In addition, the embodiments described herein provide unprecedented flexibility and customization for production sampling. Furthermore, the sampling schemes described herein do not need to be executed on the wafer inspection system. They can be executed in any off-line analysis application (with the attributes available there) or directly on a defect review tool such as a scanning electron microscope (SEM) review station. The embodiments are completely flexible and the idea is independent of the attribute space it operates on.

The embodiments described herein also introduce a new dynamic method for generating a re-normalizable sample that can be shaped with arbitrary diversification and biasing criteria to make it more efficient in capturing DOIs. For example, in one embodiment, the identifying step may include identifying a first set of defects having the most diversity in the values of the at least one attribute and modifying the first set of defects based on one or more biasing parameters to produce the set of defects. One example of potential biasing criteria is to bias the sample towards large (or small) values of particular defect attribute(s). Another example of potential biasing criteria, is to bias the sample away from a region of relatively high defect density in some portion of the feature space, e.g., spatial clusters or clouds in defect sizes and intensities, etc. An additional example of potential biasing criteria is to bias the sample away from particular regions of the feature space.

The idea of using such diversification (and possibly biasing) criteria to only create the sample bins (tiles) instead of generating the sample directly is believed to be new. Therefore, the step of generating the different tiles described herein achieves three major improvements over current methods. For example, the important aspect of diversification (and possibly biasing), namely its ability to sample defects that stand out (outliers), is preserved in this approach of generating sample bins because the defects that stand out will be in relatively low populated tiles (possibly alone) and thus are likely to be sampled or defects similar to them are guaranteed to be sampled. In this manner, the identifying, generating the different tiles, separating, and randomly selecting steps described herein may cause the created defect sample to include all types of the defects detected on the wafer. In addition, the randomly selecting step described herein may include randomly selecting the one or more defects from all of the sample bins thereby ensuring that defects having the most diversity in the at least one attribute are included in the created defect sample. The second benefit of this step is, of course, the fact that randomization guarantees unbiased statistical estimates of defect type counts (i.e., renormalization). In particular, the identifying, generating the different tiles, separating, and randomly selecting steps described herein cause the created defect sample to be statistically unbiased. The third benefit is the dynamic nature of the sample bins, whose content and distribution adapts to the data variations. This adaptive property (along with re-normalizability) makes the sample stable with respect to random fluctuations and noise floor shifts, but it also makes it substantially capable of detecting new defect types.

The acquiring, identifying, generating the different tiles, separating, randomly selecting, and creating steps described above are performed by a computer system, which may be configured as described herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 4:
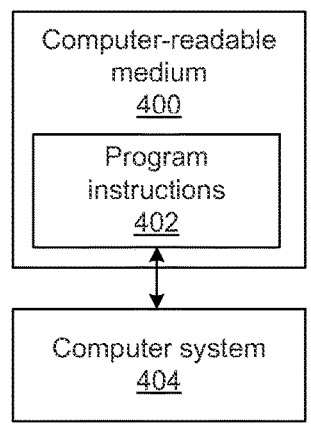
FIG. 4 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for generating a defect sample for a wafer. One such embodiment is shown in FIG. 4. In particular, as shown in FIG. 4, computer-readable medium 400 includes program instructions 402 executable on computer system 404. The computer-implemented method includes the steps of the method described above. The computer-implemented method for which the program instructions are executable may include any other step(s) described herein.

Program instructions 402 implementing methods such as those described herein may be stored on computer-readable medium 400. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 5:
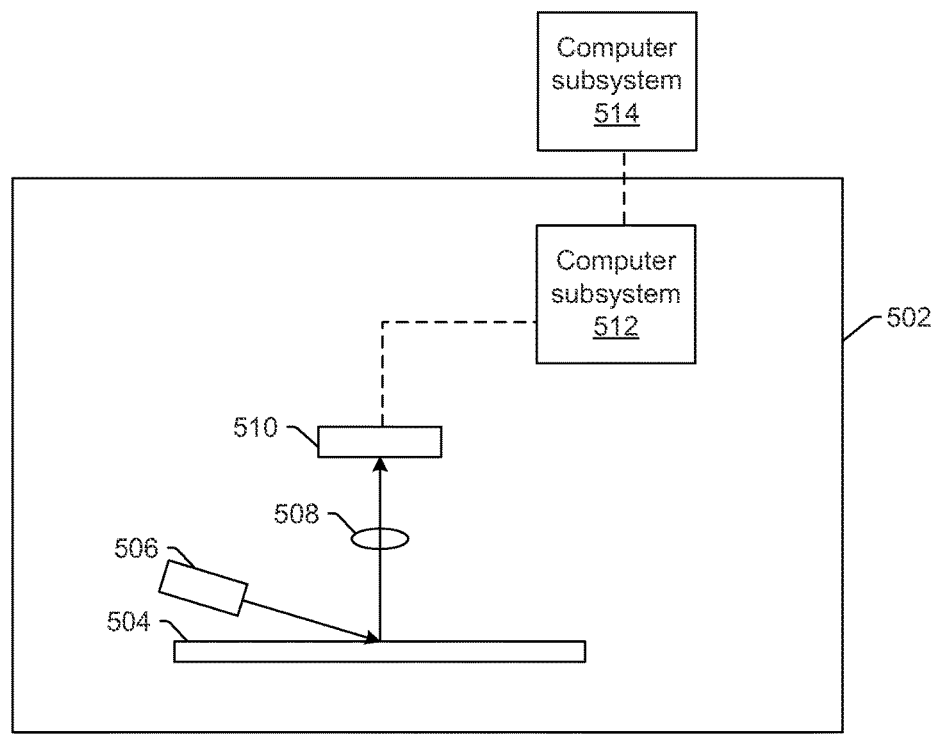
FIG. 5 is a schematic diagram illustrating a side view of one embodiment of a system configured to generate a defect sample for a wafer.

An additional embodiment relates to a system configured to generate a defect sample for a wafer. One embodiment of such a system is shown in FIG. 5. The system includes inspection subsystem 502 configured to acquire inspection results for wafer 504. The inspection results include information for defects detected on the wafer by an inspection process performed by the inspection subsystem, and the information includes information for one or more attributes of the defects. The inspection results may include any such information described herein.

The inspection subsystem includes source 506 that may include any suitable light source in the case of an optical or light-based inspection subsystem. Although the inspection subsystem will be described further herein with respect to a light-based inspection subsystem, the inspection subsystem may be modified in any suitable manner or replaced to make it an electron beam-based inspection subsystem.

Light from the light source may be directed to wafer 504. The light source may be coupled to any other suitable elements (not shown) such as one or more condensing lenses, collimating lenses, relay lenses, objective lenses, apertures, spectral filters, polarizing components and the like. As shown in FIG. 5, the light may be directed to the wafer at an oblique angle of incidence. However, the light may be directed to the wafer at an suitable angle of incidence including near normal and normal incidence, in addition, the light or multiple light beams may be directed to the wafer at more than one angle of incidence sequentially or simultaneously.

Wafer 504 may disposed upon a stage (not shown) while the light is being directed to the wafer. The stage may include any suitable mechanical or robotic assembly and may be configured to move the wafer in one or more directions while the light is being directed to the wafer such that the light can be scanned over the wafer by the inspection subsystem. However, the inspection subsystem may be configured to scan the light over the wafer in any other suitable manner.

The inspection subsystem also includes collector 508 configured to collect light scattered from the wafer (in the case of a dark field capable inspection system), which is configured to direct the collected light to detector 510 that is configured to detect the light scattered from the wafer that is collected by the collector. The collector may include any suitable number and configuration of reflective and/or refractive optical elements. Detector 510 may include any suitable detector. Detector 510 and collector 508 may therefore form at least a portion of a detection subsystem of the inspection subsystem. The detection subsystem may include one or more other suitable elements (not shown) positioned in the optical path between the detector and the wafer such as objective lenses, relay lenses, magnification lenses, zooming lenses, apertures, spectral filters, gratings, and polarizing components. Although the inspection subsystem is shown in FIG. 5 to detect light scattered from the wafer, the inspection subsystem may also or alternatively be configured for bright field (BF) inspection of the wafer. The inspection subsystem may also include more than one detector (not shown), which may be used to detect different light from the wafer simultaneously or sequentially.

The inspection subsystem may include computer subsystem 512 configured to generate the inspection results described herein. For example, computer subsystem 512 may be coupled to detector 510 by one or more transmission media (not shown), which may include "wired" and/or "wireless" transmission media such that the computer subsystem can receive the output of the detector. The computer subsystem may then use the output to detect defects on the wafer as described herein and to determine any of multiple attributes of the defects. Information generated by computer subsystem 512 may then be output by the computer subsystem in the form of an inspection results file as described further herein.

The inspection subsystem may include one computer subsystem that is configured to detect the defects on the wafer, and the system may include another, different computer subsystem that is configured to perform the steps of the methods described herein. For example, the system may include computer subsystem 514 that may be coupled to computer subsystem 512 as described above such that computer subsystem 514 can receive the inspection results from computer subsystem 512. Computer subsystem 514 is configured for performing the identifying, generating the different tiles, separating, randomly selecting, and creating steps described herein, which may be performed as described herein. The computer subsystem and the system may be configured to perform any other step(s) described herein and may be further configured as described herein. In addition, the system may include only one computer subsystem (e.g., only computer subsystem 512) that is configured to perform all of the step(s) described herein. This may be the case when an inspection tool is configured to perform the method embodiments described herein. For example, the inspection subsystem shown in FIG. 5 may be configured as an inspection tool that both detects defects on the wafer and creates a defect sample as described herein.

It is noted that FIG. 5 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the Puma 90xx, 91xx, and 93xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for creating a defect sample for a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for generating a defect sample for a wafer, comprising:

generating output for a wafer with an inspection subsystem by performing an inspection process on the wafer, wherein performing the inspection process comprises directing light from a light source of the inspection subsystem to the wafer, scanning the light over the wafer, collecting light from the wafer with a collector of the inspection subsystem, and directing the collected light from the collector to a detector of the inspection subsystem that detects the collected light and generates the output responsive thereto;

generating inspection results for the wafer with one or more computer subsystems by detecting defects on the wafer using the output generated by the detector and determining information for the defects detected on the wafer using the output generated by the detector for the defects, wherein the information comprises information for one or more attributes of the defects;

identifying a set of the defects having the most diversity in values of at least one of the one or more attributes;

generating different tiles for different defects in the set, wherein generating the different tiles comprises:

generating a tile for a first defect in the set, wherein the tile defines a portion of all of the values for the at least one attribute of all of the defects detected on the wafer, wherein the values in the portion are closer to the values for the at least one attribute of the first defect than the values for the at least one attribute of other defects in the set, and wherein the portion of said all of the values for the at least one attribute of said all of the defects detected on the wafer defined by the tile comprises the values for the at least one attribute of the first defect and other values for the at least one attribute; and repeating the generating the tile step for one or more of the other defects;

separating the defects detected on the wafer into sample bins corresponding to the different tiles based on the values of the at least one attribute of the defects and the portions of the values defined by the different tiles;

randomly selecting one or more defects from each of two or more of the sample bins; and creating a defect sample for the wafer comprising the randomly selected defects, wherein said identifying, said generating the different tiles, said separating, said randomly selecting, and said creating are performed by the one or more computer subsystems.

2. The method of claim 1, wherein the wafer is a production wafer, and wherein the inspection process is performed for production monitoring.

3. The method of claim 1, further comprising classifying the randomly selected defects in the defect sample and re-normalizing the defects detected on the wafer with results of said classifying and total number of defects in each of the sample bins thereby determining estimates of defect counts for different defect types detected on the wafer in the inspection process.

4. The method of claim 3, further comprising performing production monitoring based on the re-normalized defects.

5. The method of claim 1, further comprising performing production monitoring based on a number of the defects separated into at least one of the sample bins.

6. The method of claim 1, wherein the sample bins are not tuned bins and are not produced by a tuned defect classifier.

7. The method of claim 1, wherein said identifying, said generating the different tiles, said separating, and said randomly selecting cause the created defect sample to include all types of the defects detected on the wafer.

8. The method of claim 1, wherein said identifying, said generating the different tiles, said separating, and said randomly selecting cause the created defect sample to be statistically unbiased.

9. The method of claim 1, wherein said identifying and said generating the different tiles automatically adjust the created defect sample to a noise floor of the inspection process.

10. The method of claim 1, wherein said identifying and said generating the different tiles automatically adjust the created defect sample to wafer-to-wafer variations of the inspection process.

11. The method of claim 1, wherein said identifying comprises identifying a first set of defects having the most diversity in the values of the at least one attribute and modifying the first set of defects based on one or more biasing parameters to produce the set of defects.

12. The method of claim 1, wherein the at least one attribute does not include only positions of the defects on the wafer.

13. The method of claim 1, wherein a number of the different tiles that are generated is equal to a number of the defects in the set.

14. The method of claim 1, wherein an average number of the one or more defects randomly selected from each of the two or more of the sample bins is selected by a user.

15. The method of claim 1, further comprising determining a number of the one or more defects to be randomly selected from each of the two or more of the sample bins by dividing a total number of defects to be included in the created defect sample equally across the sample bins.

16. The method of claim 1, further comprising determining a number of the one or more defects to be randomly selected from each of the two or more of the sample bins by dividing a total number of defects to be included in the created defect sample proportionally across the sample bins.

17. The method of claim 1, further comprising determining a number of the one or more defects to be randomly selected from each of the two or more of the sample bins by dividing a total number of defects to be included in the created defect sample semi-proportionally across the sample bins.

18. The method of claim 1, further comprising determining a number of the one or more defects to be randomly selected from each of the two or more of the sample bins based on a total number of defects to be included in the created defect sample and a predetermined confidence level for using the created defect sample to re-normalize the defects detected on the wafer by the inspection process.

19. The method of claim 1, wherein said randomly selecting comprises randomly selecting the one or more defects from all of the sample bins thereby ensuring that defects having the most diversity in the at least one attribute are included in the created defect sample.

20. The method of claim 1, wherein said randomly selecting is performed for one of the two or more sample bins such that each defect in the one sample bin has an equal probability of being selected.

21. The method of claim 1, wherein said randomly selecting is performed for one of the two or more sample bins such that at least two defects in the one sample bin have different probabilities of being selected.

22. A non-transitory computer-readable medium, storing program instructions executable on one or more computer subsystems for performing a computer-implemented method for generating a defect sample for a wafer, wherein the computer-implemented method comprises:

generating output for a wafer with an inspection subsystem by performing an inspection process on the wafer, wherein performing the inspection process comprises directing light from a light source of the inspection subsystem to the wafer, scanning the light over the wafer, collecting light from the wafer with a collector of the inspection subsystem, and directing the collected light from the collector to a detector of the inspection subsystem that detects the collected light and generates the output responsive thereto;

generating inspection results for the wafer with the one or more computer subsystems by detecting defects on the wafer using the output generated by the detector and determining information for the defects detected on the wafer using the output generated by the detector for the defects, wherein the information comprises information for one or more attributes of the defects;

identifying a set of the defects having the most diversity in values of at least one of the one or more attributes;

generating different tiles for different defects in the set, wherein generating the different tiles comprises:

generating a tile for a first defect in the set, wherein the tile defines a portion of all of the values for the at least one attribute of all of the defects detected on the wafer, wherein the values in the portion are closer to the values for the at least one attribute of the first defect than the values for the at least one attribute of other defects in the set, and wherein the portion of said all of the values for the at least one attribute of said all of the defects detected on the wafer defined by the tile comprises the values for the at least one attribute of the first defect and other values for the at least one attribute; and repeating the generating the tile step for one or more of the other defects;

separating the defects detected on the wafer into sample bins corresponding to the different tiles based on the values of the at least one attribute of the defects and the portions of the values defined by the different tiles;

randomly selecting one or more defects from each of two or more of the sample bins; and creating a defect sample for the wafer comprising the randomly selected defects.

23. A system configured to generate a defect sample for a wafer, comprising:

an inspection subsystem configured to generate output for a wafer by performing an inspection process on the wafer, wherein performing the inspection process comprises directing light from a light source of the inspection subsystem to the wafer, scanning the light over the wafer, collecting light from the wafer with a collector of the inspection subsystem, and directing the collected light from the collector to a detector of the inspection subsystem that detects the collected light and generates the output responsive thereto; and one or more computer subsystems configured for:

generating inspection results for the wafer by detecting defects on the wafer using the output generated by the detector and determining information for the defects detected on the wafer using the output generated by the detector for the defects, wherein the information comprises information for one or more attributes of the defects;

identifying a set of the defects having the most diversity in values of at least one of the one or more attributes;

generating different tiles for different defects in the set, wherein generating the different tiles comprises:

generating a tile for a first defect in the set, wherein the tile defines a portion of all of the values for the at least one attribute of all of the defects detected on the wafer, wherein the values in the portion are closer to the values for the at least one attribute of the first defect than the values for the at least one attribute of other defects in the set, and wherein the portion of said all of the values for the at least one attribute of said all of the defects detected on the wafer defined by the tile comprises the values for the at least one attribute of the first defect and other values for the at least one attribute; and repeating the generating the tile step for one or more of the other defects;

separating the defects detected on the wafer into sample bins corresponding to the different tiles based on the values of the at least one attribute of the defects and the portions of the values defined by the different tiles;

randomly selecting one or more defects from each of two or more of the sample bins; and creating a defect sample for the wafer comprising the randomly selected defects.

24. The system of claim 23, wherein the wafer is a production wafer, and wherein the inspection process is performed for production monitoring.

25. The system of claim 23, wherein the one or more computer subsystems are further configured for classifying the randomly selected defects in the defect sample and re-normalizing the defects detected on the wafer with results of said classifying and total number of defects in each of the sample bins thereby determining estimates of defect counts for different defect types detected on the wafer in the inspection process.

26. The system of claim 25, wherein the one or more computer subsystems are further configured for performing production monitoring based on the re-normalized defects.

27. The system of claim 23, wherein the one or more computer subsystems are further configured for performing production monitoring based on a number of the defects separated into at least one of the sample bins.

28. The system of claim 23, wherein the sample bins are not tuned bins and are not produced by a tuned defect classifier.

29. The system of claim 23, wherein said identifying, said generating the different tiles, said separating, and said randomly selecting cause the created defect sample to include all types of the defects detected on the wafer.

30. The system of claim 23, wherein said identifying, said generating the different tiles, said separating, and said randomly selecting cause the created defect sample to be statistically unbiased.

31. The system of claim 23, wherein said identifying and said generating the different tiles automatically adjust the created defect sample to a noise floor of the inspection process.

32. The system of claim 3, wherein said identifying and said generating the different tiles automatically adjust the created defect sample to wafer-to-wafer variations of the inspection process.

33. The system of claim 23, wherein said identifying comprises identifying a first set of defects having the most diversity in the values of the at least one attribute and modifying the first set of defects based on one or more biasing parameters to produce the set of defects.

34. The system of claim 23, wherein the at least one attribute does not include only positions of the defects on the wafer.

35. The system of claim 23, wherein a number of the different tiles that are generated is equal to a number of the defects in the set.

36. The system of claim 23, wherein an average number of the one or more defects randomly selected from each of the two or more of the sample bins is selected by a user.

37. The system of claim 23, wherein the one or more computer subsystems are further configured for determining a number of the one or more defects to be randomly selected from each of the two or more of the sample bins by dividing a total number of defects to be included in the created defect sample equally across the sample bins.

38. The system of claim 23, wherein the one or more computer subsystems are further configured for determining a number of the one or more defects to be randomly selected from each of the two or more of the sample bins by dividing a total number of detects to be included in the created defect sample proportionally across the sample bins.

39. The system of claim 23, wherein the one or more computer subsystems are further configured for determining a number of the one or more defects to be randomly selected from each of the two or more of the sample bins by dividing a total number of defects to be included in the created defect sample semi-proportionally across the sample bins.

40. The system of claim 23, wherein the one or more computer subsystems are further configured for determining a number of the one or more defects to be randomly selected from each of the two or more of the sample bins based on a total number of defects to be included in the created defect sample and a predetermined confidence level for using the created defect sample to re-normalize the defects detected on the wafer by the inspection process.

41. The system of claim 23, wherein said randomly selecting comprises randomly selecting the one or more defects from all of the sample bins thereby ensuring that defects having the most diversity in the at least one attribute are included in the created defect sample.

42. The system of claim 23, wherein said randomly selecting is performed for one of the two or more sample bins such that each defect in the one sample bin has an equal probability of being selected.

43. The system of claim 23, wherein said randomly selecting is performed for one of the two or more sample bins such that at least two defects in the one sample bin have different probabilities of being selected.

* * * * *